United States Patent
Panchura et al.

(10) Patent No.: US 9,531,699 B2
(45) Date of Patent: Dec. 27, 2016

(54) ELECTRONIC PROTECTED HEALTH INFORMATION SECURITY FOR DIGITAL MEDICAL TREATMENT ROOM

(71) Applicant: KARL STORZ ENDOSCOPY-AMERICA, INC., El Segundo, CA (US)

(72) Inventors: Carly A. Panchura, Venice, CA (US); Michael Bressack, Redondo Beach, CA (US)

(73) Assignee: Karl Storz Endoscopy-America, Inc., El Segundo, CA (US)

( * ) Notice: Subject to any disclaimer, the term of this patent is extended or adjusted under 35 U.S.C. 154(b) by 0 days.

(21) Appl. No.: 14/525,686

(22) Filed: Oct. 28, 2014

(65) Prior Publication Data

US 2016/0119305 A1    Apr. 28, 2016

(51) Int. Cl.
| | |
|---|---|
| *G06F 21/00* | (2013.01) |
| *H04L 29/06* | (2006.01) |
| *G06F 21/62* | (2013.01) |
| *A61B 1/00* | (2006.01) |
| *G06F 19/00* | (2011.01) |
| *G06Q 30/00* | (2012.01) |

(52) U.S. Cl.
CPC ............ *H04L 63/08* (2013.01); *A61B 1/0002* (2013.01); *A61B 1/00039* (2013.01); *G06F 19/321* (2013.01); *G06F 21/6245* (2013.01); *H04L 63/0861* (2013.01); *G06Q 30/01* (2013.01)

(58) Field of Classification Search
CPC ....................................................... G06F 21/00
See application file for complete search history.

(56) References Cited

U.S. PATENT DOCUMENTS

| 8,069,420 B2 | 11/2011 | Plummer | |
|---|---|---|---|
| 2006/0025670 A1* | 2/2006 | Kim | A61B 3/00 600/407 |
| 2010/0094649 A1* | 4/2010 | White | G06F 19/324 705/2 |

(Continued)

OTHER PUBLICATIONS

Stryker Endoscopy; SDC3 Upcoming Features; HD Information Management System;Reference No. 0240060100; May 2012; pp. 92.

*Primary Examiner* — Jeffrey Pwu
*Assistant Examiner* — Helai Salehi
(74) *Attorney, Agent, or Firm* — Whitmyer IP Group LLC

(57) ABSTRACT

A medical imaging system includes a data store having stored medical imaging data and a computer. The system may be in a medical treatment room and is adapted to receive and display imaging data from a medical procedure. The computer has a graphical user interface that receives authentication credentials. An authenticator alternately prevents or allows a user access by logging the user into the system using the authentication credentials. A file accessor receives received medical imaging data and stores it in the data store, and retrieves the stored medical imaging data and provides it to the graphical user interface for display. Documentation data is received through the graphical user interface and is stored in the data store without requiring the user to provide the authentication credentials or be logged into the system. The user cannot access the stored medical imaging data before providing the authentication credentials and being logged into the system.

17 Claims, 2 Drawing Sheets

(56) References Cited

U.S. PATENT DOCUMENTS

2011/0227856 A1\* 9/2011 Corroy ................ H04B 13/005
  345/173
2015/0046818 A1\* 2/2015 Wade .................... A61B 19/56
  715/719

\* cited by examiner

ELECTRONIC PROTECTED HEALTH INFORMATION SECURITY FOR DIGITAL MEDICAL TREATMENT ROOM

FIELD OF THE INVENTION

The present teachings relate generally to managing information and, more particularly, to securely managing electronic protected health information (ePHI).

BACKGROUND OF THE INVENTION

A wide variety of medical imaging systems are used for performing diagnostic and surgical procedures in medical treatment rooms. Such systems have been developed to increase a surgeon's ability to perform surgery by providing intra-operative images of anatomical structures within a patient's body. During various types of minimally invasive surgeries like endoscopic, arthroscopic, and laparoscopic procedures, a surgeon is able to visually examine the interior of an organ or joint while conducting the surgery.

Medical imaging systems are known to incorporate various audiovisual devices to allow better monitoring of a medical procedure. These systems allow the surgeon, or other individuals assisting or observing, to utilize the imaging capabilities in different ways, simultaneously or at different times, for a variety of different objectives. One such system is disclosed in U.S. Pat. No. 8,069,420 to Plummer, the content of which is incorporated by reference in its entirety. As discussed therein, both still images and live video are acquired during the surgery and can be output to various different screens or recording devices.

Recent legislation has made the protection of such still images and live video, e.g., electronic protected health information (ePHI), a priority. For example, one piece of legislation is the Health Information Technology for Economic and Clinical Health Act (HITECH Act) of the American Recovery and Reinvestment Act of 2009. One requirement of that legislation is the privacy and security of electronic health information, including the requirement that HIPAA covered entities report certain data breaches. Accordingly, medical professionals are trying to comply with such legislation when using medical imaging systems to create, securely transmit and store ePHI.

In order to comply with privacy and security objectives, current medical imaging systems have implemented security features that prevent accessing any features of an imaging system before a user is authenticated. However, such security features often compromise current workflows and make medical imaging systems less user-friendly. Therefore, it would be beneficial to have a superior system and method for electronic protected health information security for digital medical treatment rooms.

SUMMARY OF THE INVENTION

The needs set forth herein as well as further and other needs and advantages are addressed by the present embodiments, which illustrate solutions and advantages described below.

The system of the present embodiment includes, but is not limited to, a computer in communication with a data store having stored medical imaging data. The computer has a graphical user interface receiving user data from a user, the user data including authentication credentials used to allow the user access to predetermined system resources, an authenticator alternately preventing or allowing the user access to the predetermined system resources by logging the user into the system using the authentication credentials, and a file accessor receiving received medical imaging data and storing the received medical imaging data in the data store, and retrieving the stored medical imaging data from the data store and providing it to the graphical user interface for display to the user. An endoscope provides the received medical imaging data and a touch screen displays the graphical user interface. The medical imaging system may be in an operating room and is adapted to receive and display imaging data from a medical procedure. Documentation data is received from the user through the graphical user interface and is stored in the data store without requiring the user to provide the authentication credentials or be logged into the system, the documentation data concerning information about the medical procedure. The user cannot access the stored medical imaging data before providing the authentication credentials and being logged into the system. The user is logged out of the system after a predetermined amount of time of system inactivity, the predetermined amount of time configurable by the user using the graphical user interface.

In another embodiment the system includes, but is not limited to, a computer in communication with a data store having stored medical imaging data. The computer has a graphical user interface receiving user data from a user, the user data including authentication credentials used to allow the user access to predetermined system resources, an authenticator alternately preventing or allowing the user access to the predetermined system resources by logging the user into the system using the authentication credentials, and a file accessor receiving received medical imaging data and storing the received medical imaging data in the data store, and retrieving the stored medical imaging data from the data store and providing it to the graphical user interface for display to the user. The medical imaging system may be in an operating room and is adapted to receive and display imaging data from a medical procedure. Documentation data may be received from the user through the graphical user interface and is stored in the data store without requiring the user to provide the authentication credentials or be logged into the system, the documentation data concerning information about the medical procedure. The user cannot access the stored medical imaging data before providing the authentication credentials and being logged into the system.

The method of the present embodiment includes the steps, but is not limited to, receiving documentation data from a user through a graphical user interface and storing the documentation data in a data store without requiring the user to provide authentication credentials or be logged into the system, the documentation data concerning information about the medical procedure, retrieving the stored medical imaging data and providing it to the graphical user interface for display to the user only after the user provides the authentication credentials and is logged into the system, and logging the user out of the system after a predetermined amount of time of system inactivity.

Other embodiments of the system and method are described in detail below and are also part of the present teachings.

For a better understanding of the present embodiments, together with other and further aspects thereof, reference is made to the accompanying drawings and detailed description, and its scope will be pointed out in the appended claims.

DETAILED DESCRIPTION OF THE INVENTION

Figure 1:
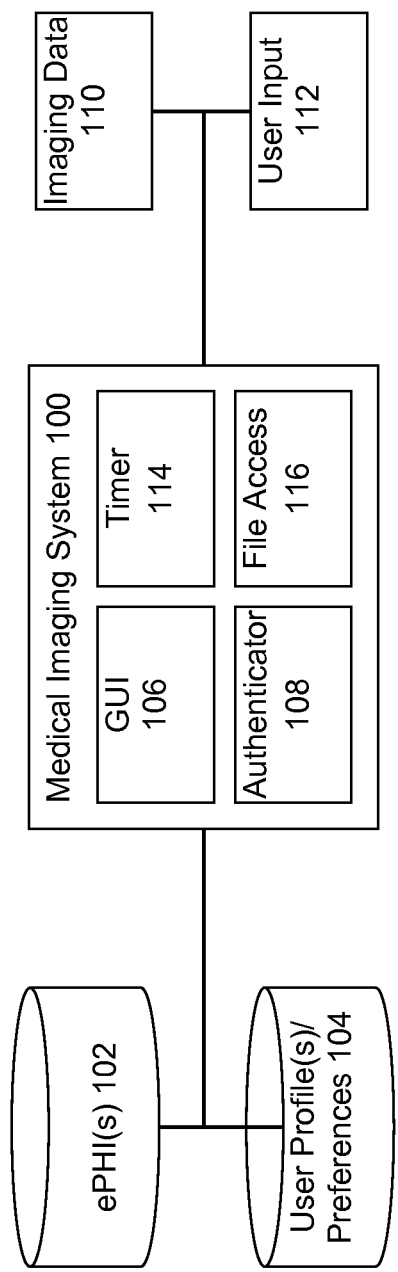
FIG. 1 is one embodiment of a medical imaging system according to the present teachings.

The present teachings are described more fully hereinafter with reference to the accompanying drawings, in which the present embodiments are shown. The following description is presented for illustrative purposes only and the present teachings should not be limited to these embodiments. Any computer configuration and architecture satisfying the speed and interface requirements herein described may be suitable for implementing the system and method of the present embodiments.

The assignee of the present application is a provider of medical image capture solutions that manage ePHI (e.g., KARL STORZ®'s OR1 Fusion™, AIDA HD Connect™, AIDA Compact™, etc.). These imaging systems provide a number of benefits. For example, they have central image and data archiving systems that make documentation more convenient and comprehensive, as well as allow editing and marking of image and video files.

Medical imaging systems are used with compatible endoscopic and general surgery devices. For example, they are used in general laparoscopy, nasopharyngoscopy, ear endoscopy, sinuscopy, and plastic surgery wherever a laparoscope/endoscope/arthroscope is indicated for use, although not limited thereto. Users include general surgeons, nurses, and other medical professionals, among others.

Generally, a medical imaging system is a computer-based unit that records, manages, and archives digital images and videos of surgical procedures. It can simplify file management by recording surgical photos and videos to compact digital media, such as CDs, DVDs, Compact Flash Cards, USB Hard Drive, or USB storage devices, which may then be viewed from a personal computer, a DVD player, or from the system itself. The medical imaging system typically records images and videos on a built-in hard drive, where they can be easily accessed after the surgical procedure. The media stored on the hard drive can be tagged with patient-specific information and saved to digital media using a touch screen control panel. This media can also be sent at the push of a button to another computer (such as a server) for long-term storage and browser-based accessibility, although not limited thereto.

In order to comply with recent privacy and security legislation, providers of medical imaging systems have implemented certain security features. For example, known systems require that a user login to the system before performing any task on the system (or worse have no security). However, such features may adversely affect system usability. An imaging system may also log a user out of the system after a predetermined amount of time (e.g., a "timeout" feature). Because systems require a user to be logged into the system (e.g., authenticated) before using it, users of those systems will have to log back in after a timeout occurs.

In use, ePHI may be stored on the medical imaging system in an electronic "filing cabinet." To access the filing cabinet a user selects the icon through the medical imaging system's graphical user interface (GUI) and a dialog box may ask for a username and password. Once the user enters a valid username and password they may have access to the stored ePHI. After an idle time, the system may automatically log the user out to protect the ePHI.

To address some of the shortcomings with known systems, it is preferable to make the timeout period configurable so the user can set the length of time, as well as whether to enable or disable the timeout feature. When the timeout feature is disabled, the system (and the ePHI) is accessible once a user is logged into the system. In addition, it is preferable that a user can start use of the system (e.g., patient documentation, recording imagery from a procedure, etc.) without first logging into the system. This simplifies a user's workflow by removing the requirement of logging in to begin adding information to the system. To access ePHI stored in the filing cabinet, however, the system may still require input of a username and password in order to comply with security and privacy policies. When nothing is occurring (e.g., no images/videos are being recorded and no one is interacting with the system), the system may log out the current user, thus providing additional protection of patient electronic health information.

As used herein, the term "documentation" generally refers to capturing information about a patient and/or a procedure, although not limited thereto. A patient "case" may first be documented (e.g., created) in the system so that it can be associated with any pictures or video captured during the procedure. The case may be created, accessed, modified, and saved to the system's hard disk or to external media, such as USB drives, CD/DVD, or network servers. Documentation may include providing the following information, although not limited thereto: patient name, patient ID, patient gender, patient birth date, surgeon, referrer, specialty, procedure, procedure date, notes, accession number, facility, station, department, etc. Images and video can then be captured and associated with the patient case In further embodiments, other authentication features may be incorporated. For example, biometrics (e.g., fingerprint, iris, voice, etc.) and digital signatures may be used, although not limited thereto. However, use of the present teachings with a traditional username/password combination may present an easier, more efficient, and less costly system. The only change for a medical professional may be a process change to enforce log out policies.

Referring now to FIG. 1, shown is one embodiment of a medical imaging system according to the present teachings. The medical imaging system 100 includes a computer executing software components stored on computer readable media. Imaging data 110 may be provided to the system from a plurality of sources, for example, endoscopes, room cameras, etc. Imaging data may be stored in an ePHI data store 102 accessible by the system.

The medical imaging system 100 also may include a graphical user interface (GUI) 106 that allows a user to interact and control the system with user input 112, for example, using a touch screen. Users may store user profiles and preferences in a data store 104. For example, the data store 104 may have username/password information that the authenticator 108 uses to authenticate a user and log them into the system before providing the user access to stored ePHI 102. Users may also have preferences such as whether a timeout feature is enabled/disabled, and the timeout period after which a user is logged out the system, as determined by a timer 114.

A file access component 116 (also referred to as "file accessor") may control access (e.g., saving, retrieving, etc.) to ePHI 102. Typically, image data for patient cases is automatically saved (e.g., archived) in the data store 102 of the medical imaging system 100. These cases may be accessible through the GUI 106 by means of a filing cabinet icon or some other identifier. Users may also access various other network locations or removable media (e.g., USB, DVDs, etc.), although not limited thereto. A user may be presented with a list of cases, which may include patent information (e.g., ID, name, etc.) as well as procedure information (e.g., surgeon, procedure name, date/time, etc.). Once a user selects a patient case, the system may play the images/video for the selected case.

Sources of imaging data 110 provided to the system 100 may include any devices, systems, or networks that generate, acquire, store, monitor, or control still images or video. For example, the sources may include image acquisition devices such as endoscopic cameras, video endoscopes, room cameras, light cameras, and boom cameras. Likewise, the sources may include any recording, storage, and/or archival devices or systems, such as traditional video cassette recorders or digital video recording devices (such as a DVD recording device), image capture devices, a PACS (Picture Archiving and Communication System) computer, or a hospital information system. Sources may also include other devices from which medical imaging data may be received, such as a patient monitor or a central computer for controlling various devices, etc.

Once a source of medical imaging data has been selected, the user may then select a particular destination from among the plurality of available destinations to receive the medical imaging data from the presently selected source by pressing a destination icon. In this way, the user may select one, some, or all of the destinations to receive the medical imaging data being supplied from the presently selected source. As each destination icon is pressed, the medical imaging data being supplied by the presently selected source and producing the images presently being viewed in the display window is communicated to the corresponding destination. In addition to selecting and controlling various sources and destinations of medical imaging data, and routing, altering, recording, and viewing that data, the user can also control several other items from the touch screen, such as documentation (e.g., creating patient cases) and image manipulation.

The destinations for the imaging data 110 supplied by the sources may include any devices, systems, or networks that display medical images generated from the medical imaging data, or otherwise communicate the medical imaging data to viewers, or store the imaging data. For example, the destinations may include any of various displays, such as, for example, a flat panel display, a plasma screen, or a computer monitor. Additionally, the destinations may include a recording device or storage device. As described above, ePHI is typically stored in a secure data store 102 accessible by the imaging system 100.

Figure 2:
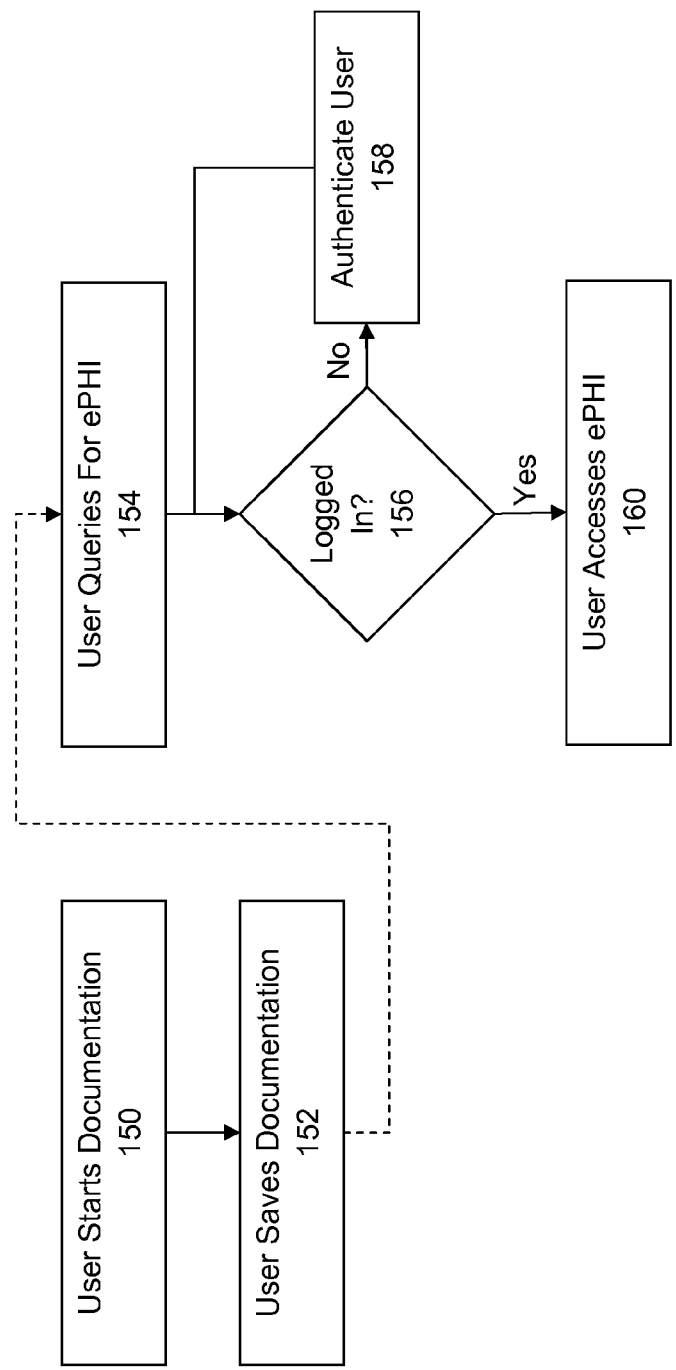
FIG. 2 is one embodiment of a flow chart of steps for using the medical imaging system according to FIG. 1.

Referring now to FIG. 2, shown is one embodiment of a flow chart of steps for using the medical imaging system according to FIG. 1. As shown, the user may first start using the system 150 without being prompted for login information. This may include beginning documentation on a patient/procedure/etc., or beginning to capture imagery from an imaging source, although not limited thereto. At this point user authentication may not be necessary.

The documentation (or other data) may then be saved 152 in the medical imaging system (e.g., data store 102 shown in FIG. 1). When the user then tries to retrieve 154 that data (or other ePHI saved in the system), the system will determine if the user is logged in 156. If not, the user will be authenticated 158 by getting their username/password combination or some other authentication (e.g., biometrics). Once the user is authenticated they may be provided with stored ePHI 160. Authenticating the user before allowing the user to retrieve stored ePHI may satisfy security and privacy goals.

With current medical imaging systems, the workflow for using a medical imaging system is as follows:
1. Login
2. Enter patient information
3. Capture images/video
4. Archive (e.g., USB, DVD, network storage, etc.)

Once a user is logged in they can go into the filing cabinet and basically see everything. However, the user may be prevented from other system functionality without first logging in, including the documentation of a new patient/procedure/etc. or beginning to capture new image data, etc. It may be preferable to allow a user to access certain functionality of the system that does not jeopardize the security of stored ePHI.

In accordance with the present teachings, system usability may be increased without decreasing the security of ePHI. Without logging into the system the staff and surgeon can immediately start using the system. For general use of documentation of surgeries in the OR, it may be used by hospitals trying to better enforce greater protection of their patient's electronic health information. When and if they want to review ePHI that is stored in the filing cabinet they can enter a username and password.

Accordingly, with a medical imaging system according to the present teachings the workflow may be as follows:
1. Enter patient information
2. Capture images/video
3. Archive (e.g., USB, DVD, network storage, etc.)

No login may be required to start documentation (or certain other tasks). If a user wants to view procedures in the filing cabinet, however, they may have to login (e.g., login dialog box appears after selecting filing cabinet icon) to comply with security/privacy policies.

In another example, the workflow for a medical imaging system according to the present teachings may be as follows:
1. Enter patient information
2. Capture images/video
3. Archive (e.g., USB, DVD, network storage, etc.).
4. The user leaves the room and the system remains ON.
5. After a pre-determined period of time of inactivity, the system displays a message which reads "Are you finished documenting [Patient Information]?
6. If yes, the case is finalized. If no, the user is able to continue documentation.

In this way, the system keeps two consecutive patient surgeries from accidentally being recorded under the first patient's name.

While the present teachings have been described above in terms of specific embodiments, it is to be understood that they are not limited to these disclosed embodiments. Many modifications and other embodiments will come to mind to those skilled in the art to which this pertains, and which are intended to be and are covered by both this disclosure and the appended claims. It is intended that the scope of the present teachings should be determined by proper interpretation and construction of the appended claims and their legal equivalents, as understood by those of skill in the art relying upon the disclosure in this specification and the attached drawings.

What is claimed is:
1. A medical imaging system for use during a medical procedure, comprising:
  a data store having stored medical imaging data; a computer in communication with the data store and having:

a graphical user interface receiving user data from a user, the user data including authentication credentials used to allow the user access to predetermined system resources;

an authenticator alternately preventing or allowing the user access to the predetermined system resources by logging the user into the system using the authentication credentials;

a file accessor receiving medical imaging data and documentation data for the medical procedure, and storing the received medical imaging data and documentation data in the data store, and retrieving the stored medical imaging data and documentation data from the data store and providing the stored medical imaging data and documentation data to the graphical user interface for display to the user;

an endoscope; and a touch screen displaying the graphical user interface;

the touch screen adapted to receive the documentation data from the user through the graphical user interface without requiring the user to provide the authentication credentials or be logged into the system, the documentation data stored in the data store;

the touch screen adapted to receive a selection of the endoscope as a source of the received medical imaging data and display the received medical imaging data on the touch screen in real-time during the medical procedure without requiring the user to provide the authentication credentials or be logged into the system, the received medical imaging data stored in the data store;

the touch screen requiring the user to provide the authentication credentials or be logged into the system before permitting access to the stored medical imaging data or documentation data; and wherein the user is logged out of the system after a predetermined amount of time of system inactivity, the predetermined amount of time configurable by the user using the graphical user interface.

2. The system of claim 1 wherein using the graphical user interface the user optionally deactivates the feature that the user is logged out of the system after a predetermined amount of time of system inactivity.

3. A medical imaging system for use during a medical procedure, comprising:

a data store having stored medical imaging data; a computer in communication with the data store and having:

a graphical user interface receiving user data from a user, the user data including authentication credentials used to allow the user access to predetermined system resources;

an authenticator alternately preventing or allowing the user access to the predetermined system resources by logging the user into the system using the authentication credentials; and a file accessor receiving medical imaging data and documentation data for the medical procedure and storing the received medical imaging data and documentation data in the data store, and retrieving the stored medical imaging data and documentation data from the data store and providing the stored medical imaging data and documentation data to the graphical user interface for display to the user; and a touch screen displaying the graphical user interface; the touch screen adapted to receive the documentation data from the user through the graphical user interface without requiring the user to provide the authentication credentials or be logged into the system, the documentation data stored in the data store;

the touch screen adapted to display the received medical imaging data in real-time during the medical procedure without requiring the user to provide the authentication credentials or be logged into the system, the received medical imaging data stored in the data store;

the touch screen requiring the user to provide the authentication credentials or be logged into the system before permitting access to the stored medical imaging data or documentation data; and the user is logged out of the system after a predetermined amount of time of system inactivity, the predetermined amount of time configurable by the user using the graphical user interface.

4. The system of claim 3 further comprising a timer, wherein the user is logged out of the system after a predetermined amount of time of system inactivity as determined by the timer.

5. The system of claim 3 wherein the data store comprises a plurality of databases.

6. The system of claim 3 wherein the graphical user interface, the authenticator, and the file accessor comprise software components executing on computer readable media on the computer.

7. The system of claim 3 further comprising an endoscope providing the received medical imaging data.

8. The system of claim 3 wherein the authentication credentials comprise a username and password combination.

9. The system of claim 3 wherein the authentication credentials comprise biometric information for the user.

10. The system of claim 4 wherein the predetermined amount of time is configurable by the user using the graphical user interface.

11. The system of claim 4 wherein using the graphical user interface the user optionally deactivates the feature that the user is logged out of the system after a predetermined amount of time of system inactivity.

12. The system of claim 6 wherein the graphical user interface, the authenticator, and the file accessor comprise different software components.

13. A method of using a medical imaging system in a medical treatment room that is adapted to receive and display imaging data from a medical procedure, the medical imaging system comprising:

a data store having stored medical imaging data; a computer in communication with the data store and having:

a graphical user interface receiving user data from a user, the user data including authentication credentials used to allow the user access to predetermined system resources;

an authenticator alternately preventing or allowing the user access to the predetermined system resources by logging the user into the system using the authentication credentials; and a file accessor receiving medical imaging data and documentation data for the medical procedure and storing the received medical imaging data and documentation data in the data store, and retrieving the stored medical imaging data and documentation data from the data store and providing the stored medical imaging data and documentation data to the graphical user interface for display to the user; the method comprising:

receiving the documentation data from the user through the graphical user interface without requiring the user to provide the authentication credentials or be logged into the system, the documentation data stored in the data store:

displaying the received medical imaging data in real-time during the medical procedure without requiring the user to provide the authentication credentials or be logged into the system, the received medical imaging data stored in the data store:

retrieving the stored medical imaging data or documentation data only after the user provides the authentication credentials or is logged into the system: and logging the user out of the system after a predetermined amount of time of system inactivity.

14. The method of claim 13 wherein the predetermined amount of time is configurable by the user using the graphical user interface.

15. The method of claim 13 wherein using the graphical user interface the user optionally deactivates the feature that the user is logged out of the system after a predetermined amount of time of system inactivity.

16. The method of claim 13 wherein after a predetermined amount of time of system inactivity after the receiving documentation data has begun, the system asks the user through the graphical user interface whether documentation is complete, and if so the documentation is finalized.

17. The method of claim 13 wherein the graphical user interface is displayed on a touch screen.

* * * * *